United States Patent [19]

Hinton

[11] 4,449,527

[45] May 22, 1984

[54] ENDOTRACHEAL TUBE HOLDER

[76] Inventor: Deborah L. Hinton, 225 Virginia Dr., Hueytown, Ala. 35023

[21] Appl. No.: 313,623

[22] Filed: Oct. 21, 1981

[51] Int. Cl.³ .......................................... A61M 25/02
[52] U.S. Cl. ........................ 128/207.17; 128/DIG. 26
[58] Field of Search ..................... 128/200.26, 207.14, 128/207.17, DIG. 26

[56] References Cited

U.S. PATENT DOCUMENTS

| | | | |
|---|---|---|---|
| 2,039,142 | 4/1936 | Brehm | 128/207.17 |
| 2,908,269 | 10/1959 | Cheng | 128/207.14 X |
| 3,760,811 | 9/1973 | Andrew | 128/207.17 |
| 3,774,616 | 11/1973 | White | 128/200.26 |
| 4,249,529 | 2/1981 | Nestor et al. | 128/207.17 |
| 4,326,515 | 4/1982 | Shaffer et al. | 128/207.17 |
| 4,331,144 | 5/1982 | Wapner | 128/207.17 |
| 4,332,245 | 6/1982 | Boone, Sr. | 128/207.17 |

FOREIGN PATENT DOCUMENTS 445218  4/1936  United Kingdom ........... 128/200.26

Primary Examiner—Lee S. Cohen
Attorney, Agent, or Firm—Antonelli, Terry & Wands

[57] ABSTRACT

An endotracheal tube holder is disclosed for holding an endotracheal tube at a fixed position within a patient's mouth before, during and after surgical procedures while permitting access to and visualization of the mouth. The holder is comprised of a variable diameter clamp made from a cylindrical section which frictionally engages the endotracheal tube at a position external to the patient's mouth and is dimensioned to not obstruct access to or visualization of the interior of the mouth. A strap engages the clamp to secure the endotracheal tube to the patient to minimize longitudinal, rotational, and lateral movement of the endotracheal tube within the patient's mouth. The width of the strap in proximity to the patient's mouth is equal to or less than the outside diameter of the cylindrical section to minimize the obstruction of the patient's mouth by the strap. The annular cross section of the clamp minimizes the obstruction of the mouth by the clamp.

18 Claims, 5 Drawing Figures

ENDOTRACHEAL TUBE HOLDER

BACKGROUND OF THE INVENTION

1. Field of the Invention

The invention relates to endotracheal tube holders.

2. Description of the Prior Art

Endotracheal tubes are conventionally used to administer anesthesia or gases to the lungs before, during and after surgical procedures. Various endotracheal tube holders have been developed for the purpose of retaining an endotracheal tube within the patient's mouth before, during and after medical procedures.

It has been the widespread practice to secure an endotracheal tube within the patient's mouth by adhesive tape which engages the endotracheal tube and the face. The securing of an endotracheal tube with tape does not provide ease of access to and visualization of the patient's mouth for aspirating fluids or the administering of the treatment within the patient's mouth. An adhesive tape endotracheal tube holder may seriously irritate a patient's skin. It is difficult to rapidly disconnect and connect an endotracheal tube from a patient which has been secured with tape because of the adhesive properties of the tape. With the use of adhesive tape endotracheal tube holders, movement of the endotracheal tube is possible in the longitudinal, lateral and rotational directions which may harm the delicate tissues within the patient's trachea. Flexibility of the adhesive tape permits some movement of the endotracheal tube in the longitudinal, lateral and rotational directions. Moreover, if the tape loses adhesion from the endotracheal tube or the patient's face, the potential for harm to the delicate tissues within the trachea is increased as a consequence of movement of the endotracheal tube or the endotracheal tube may become dislodged enough to come out of the trachea.

Several endotracheal tube holders have been developed for holding endotracheal tubes in place within the mouth which are strapped to the head. These endotracheal tube holders are disclosed in U.S. Pat. Nos.: 2,820,457; 3,602,227; 3,713,448; 3,760,811; 3,774,616; 3,946,742; and 4,223,671.

The endotracheal tube holders disclosed in U.S. Pat. Nos. 2,820,457; 3,602,227; 3,760,811; 3,774,616 and 4,223,671 include structures which cover either a substantial part of or all of the opening to the mouth which makes access to and visual inspection of the mouth difficult.

The endotracheal tube holder disclosed in U.S. Pat. No. 3,946,742, which is stated to minimize the obstruction of the mouth, includes a retainer which projects into the patient's mouth. The projection of the retainer into the mouth and in contact with the teeth could interfere with access to and inspection of the mouth. Moreover, the endotracheal tube holder does not have a clamp which retains the endotracheal tube in a fixed longitudinal, lateral, and rotational position within the patient's mouth.

The endotracheal tube holder of U.S. Pat. No. 3,713,448 uses tape to secure the endotracheal tube to a pair of adapters which are secured to the ears. The endotracheal tube holder does not use a clamp to secure the endotracheal tube in a fixed position in the mouth. The tape could obstruct access to and visualization of the patient's mouth. Moreover, the tape may have sufficient flexibility to make possible longitudinal, lateral and rotational movement of the endotracheal tube.

SUMMARY OF THE INVENTION

An endotracheal tube holder should possess several characteristics. Since seconds often count during surgical procedures, it is extremely important that an endotracheal tube holder should be rapidly attachable and detachable from an endotracheal tube without the exercise of special skills. An endotracheal tube holder should permit its attachment to and detachment from the endotracheal tube without requiring disconnection and reconnection of vital gasses and anesthesia being delivered to the patient through the endotracheal tube. It is of extreme importance that the endotracheal tube holder should not restrict either visualization of or access to the interior of the patient's mouth to permit the aspiration of fluids from the interior of the mouth or the administration of other treatments nor should it allow the endotracheal tube to be dislodged and come out of the trachea. In view of the fact that medical procedures often require that the endotracheal tube must be left in place within the patient's mouth for long periods of time, an endotracheal tube holder should be designed to cause as little irritation as is possible to the tissues of the face and interior of the mouth. Finally, an endotracheal tube holder should restrain the endotracheal tube in the longitudinal (parallel to the longitudinal axis of the endotracheal tube), lateral (sideways within the patient's mouth) and rotational (angularly about the longitudinal axis of the endotracheal tube) directions to minimize injury to the interior of the patient's mouth, pharynx, larynx, trachea and main-stem bronchi.

Maintaining longitudinal stability of an endotracheal tube within the mouth is important. Longitudinal movement of the endotracheal tube into the right main-stem bronchus past the point where it is intended to be positioned can be harmful. Longitudinal movement of the endotracheal tube out of the mouth from its intended position can be a serious problem. The repositioning of the endotracheal tube after it has been pulled out of position can only be done by specially trained personnel and requires special instrumentation.

The endotracheal tube holder of the present invention has many advantages. The small number of parts, which may be manufactured from materials such as plastic, makes its manufacturing cost low. The positioning of the clamp for the endotracheal tube external to the mouth enhances access to and visualization of the patient's mouth. The width of the strap in proximity to the mouth, which is equal to or less than the outside diameter of the cylindrical clamp, enhances access to and visualization of the mouth. The preferred form of attachment of the strap to the clamp which uses a strap which is bifurcated in proximity to the point of attachment with the clamp enhances the rotational stability of the clamp within the mouth, pharynx, larynx, and trachae. The grooving of the interior surface of the cylindrical clamp ensures positive engagement of the endotracheal tube with the clamp before, during and after surgical procedures. The variable diameter clamp facilitates engagement of different diameter endotracheal tubes. The pads on the strap which contact the cheeks minimize irritation. The snap connectors located in the first ends of the sections of the strap and the loops located on the exterior surface of the clamp facilitate rapid connection and disconnection of the clamp from the strap. The "adhesive" material which is attached to the second end of each strap which is remote from the point of attachment with the clamp permits the use of the endotracheal tube holder with patients having different sized heads without time consuming adjustment. The design of the clamp allows for rapid attachment and detachment of the clamp without necessitating the disconnection of the means used to deliver gasses, anesthesia, air, etc.

An endotracheal tube holder in accordance with the invention includes a clamp comprised of a cylindrical section having an interior cylindrical clamping surface which is of variable diameter to prevent rotation of an endotracheal tube with respect to the clamp and an exterior cylindrical surface; first and second attachment means which are respectively attached to separate sections of the exterior cylindrical surface; a strap having at least first and second ends which are respectively attachable to and detachable from the first and second attachment means; the width of the first and second ends of the strap at the point of attachment to the clamp being equal to or less than the outside diameter of the cylindrical section so as to enhance access to and visualization of the patient's mouth.

DETAILED DESCRIPTION OF THE INVENTION

Figure 1:
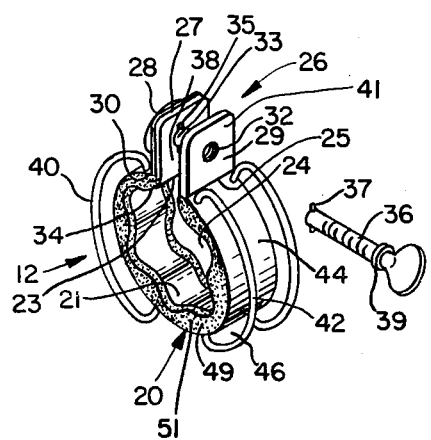
FIG. 1 is a view illustrating a clamp used in an endotracheal tube holder in accordance with the invention.

FIG. 1 illustrates the design of a variable diameter clamp 12 which may be used with the present invention. The clamp 12 is comprised of a cylindrical section 20 of a variable diameter. The cylindrical section 20 has an inner surface 21 which engages an endotracheal tube 22 (FIG. 4) which is placed in the patient's mouth. The cylindrical section is longitudinally split to form first and second ends 23 and 25. Each end 23 and 25 has first and second extensions 27 and 29 which project radially outward. The inner surface 21 has a plurality of longitudinal grooves 24 which are provided for gripping the endotracheal tube 22 tightly to prevent slippage of the endotracheal tube with respect to clamp 12 while it is in the mouth. The clamp 12 has means 26 for varying its diameter to permit gripping the endotracheal tubes 22 of different diameters which conventionally range in diameter from 3 mm to 10 mm. The means 26 for varying the diameter of the clamp 12 is comprised of a nut 28 which is attached to the first extension 27 and having a bore (not illustrated) in alignment with bore 33, which extends through the first extension, a bore 32 located in a second extension 29 of the cylinder, a keyway 35 located within the bore 33 which also extends through nut 28, and a threaded member 36, having a key 37 located at its end which is dimensioned to pass through keyway 35, that engages the nut 28. The threaded member 36 further has a flange 39 located at its other end which enages the outside surface 41 of the extension 29. The threads on the threaded member extend from the end at which flange 39 is located down to but not in engagement with the keyway 35 to permit the key 37 to pass through the keyway 35 without having the threads of the threaded member engage the threads of nut 28. The inside surface (not illustrated) of end 29 has a countersunk enlarged bore (not illustrated) which permits the end of the threaded member 36 which carries the key 37 to be pulled axially within bore 32 to not occlude the space 38 between the extensions 27 and 29. The diameter of the cylinder 20 is varied by turning the threaded member 36 which causes the space 38 to vary in dimension. First and second pairs of loops 40 and 42 are mounted on the outside surface 44 of the cylindrical section 20 at opposed positions to facilitate the attachment to and detachment of the clamp 12 from the strap 14. While a pair of loops 40 and 42 are illustrated, it should be understood that a single loop may be attached to the opposed sections of the outside surface 44 to accomplish attachment of the strap 14 to the clamp 12. A padding material 51 is secured to the annular surfaces 49 defined by the cylindrical section 20 to minimize irritation to the lips, gums or teeth of the patient. The clamp 12 may be made by the molding of a suitable plastic which is sufficiently flexible to permit adjustment of its diameter without breakage.

Figure 2:
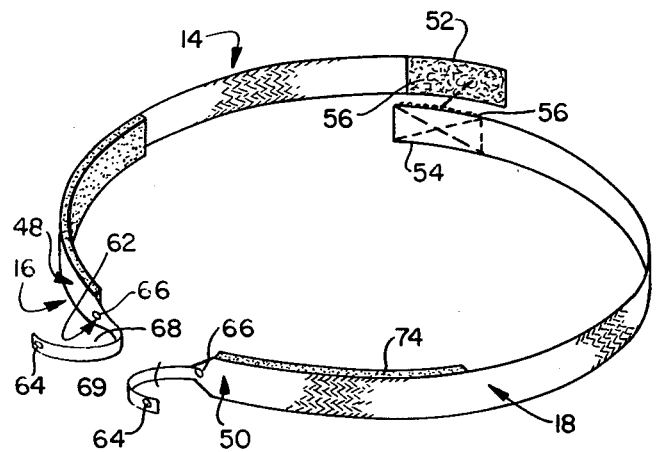
FIG. 2 is a view illustrating a strap used in accordance with the first embodiment of the present invention.
Figure 3:
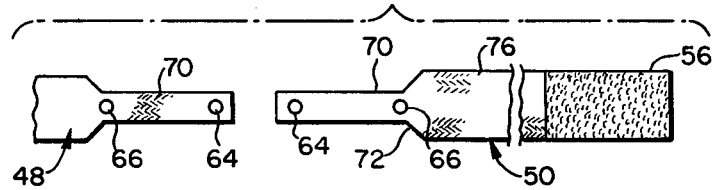
FIG. 3 is an expanded view of the ends of the strap which are illustrated in FIG. 2.

FIGS. 2 and 3 illustrate the detailed design of the strap 14 which is used for securing the clamp 12 to the patient's head. The strap 12 has two sections 16 and 18. The first end 48 of section 16 has a snap fastener 62 which forms a loop 68 upon closure. The first end 50 of section 18 has a snap 62 that forms a loop 69 upon closure. The second ends 52 and 54 each have a piece of material 56 bounded thereto which has the characteristic that it will adhere to the other corresponding piece of material 56 upon contact. A suitable material is VELCRO although other materials with this characteristic may be used. Each snap fastener 62 is comprised of ball 64 and corresponding socket 66. The loops 68 and 69 engage the first and second pairs of loops 40 and 42 (FIG. 1) when the first ends 48 and 50 of section 16 and 18 are threaded through the space 46 defined by each pair of loops 40 and 42. The snap fasteners 62 permit rapid attachment to and detachment of the strap 14 from the clamp 12.

FIG. 3 illustrates a detailed view of the ends 48 and 50 of the sections 16 and 18 which are illustrated in FIG. 1. The sections 16 and 18 of the strap 14 may be made by molding a plastic material. Sections 70 have a reduced width which is less than the width of the part of the sections 16 and 18 which contact the cheeks and the back of the head for minimizing the occulsion of the opening to the patient's mouth to facilitate access to and visualization. The width of the sections 70 should be equal to or less than the outside diameter of the cylindrical section 20 (FIG. 1). While the invention is not limited thereto, in the preferred form the overall length of the sections 16 and 18 should be approximately 14½ inches with the section 70 being approximately 2 inches in length, the tapered part 72 is approximately ½ inch in length, section is aproximately 8 inches in length and the material section 56 is approximately 4 inches in length. In the preferred form, the section 70 is approximately ½ inch in width, the tapered part 72 varied between ½ inch and 1 inch, the remainder of the sections 16 and 18 are 1 inch in width. The length of sections 70 should preferably not be shorter than 2½ inches.

Figure 4:
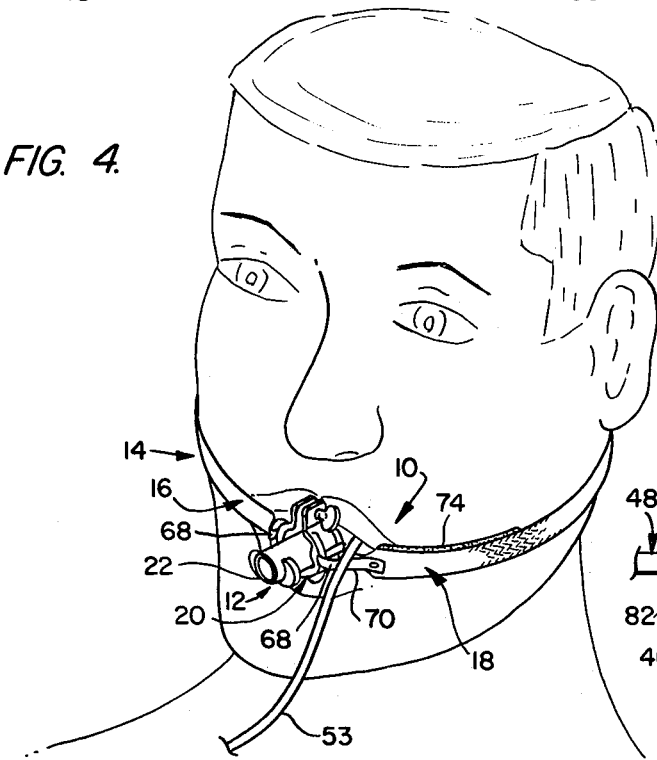
FIG. 4 is a view illustrating an endotracheal tube holder in accordance with the first embodiment of the invention as it is used to secure an endotracheal tube in the mouth of a patient undergoing a surgical procedure.

FIG. 4 illustrates an important feature of the present invention which is that the frontal area of the clamp 12 and strap 14 in proximity to the mouth is minimized to maximize access to and visualization of the interior of the patient's mouth consequent from the width of the sections 70 being equal to or less than the outside diameter of the cylindrical section 20 and the clamp 12 having annular cross section 49. Clamps of the type used in the prior art which do not have an annular frontal area do not minimize the frontal area of the clamp in proximity to the opening of the mouth.

Figure 5:
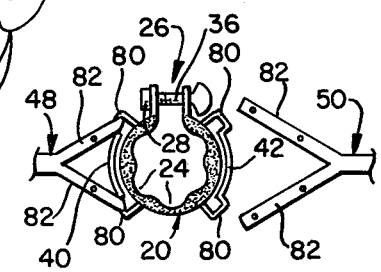
FIG. 5 is a view illustating the preferred attachment mechanism for securing the strap to the clamp.

FIG. 5 illustrates the preferred design of the mechanism for attaching the strap 14 to the clamp 12 which enhances the longitudinal, rotational, and lateral stability of the endotracheal tube 22 within the mouth over that obtainable with the embodiment of FIGS. 1–4. The design of the clamp 12 is identical to FIG. 1 with the exception that the pairs of loops 40 and 42 have been modified to contain strap retaining sections 80 which engage the bifurcated ends 82 of the first ends of the strap 48 and 50. The location of the individual strap retaining sections 80 should be angularly displaced as far as possible from each other within the loops 40 and 42 so they are in proximity to the point at which the loops project form the outside surface of the cylindrical section 20. The ease of access into the mouth for administering treatment is represented by the insertion of the tube 53 into the opening beside the endotracheal tube holder 10. Like the embodiment described with reference to FIGS. 1 and 2 supra, the width of the strap 14 in proximity to the pairs of loops 40 and 42 should be equal to or less than the outside diameter of clamp 12 to minimize the occlusion of the mouth opening with the strap. The bifurcated ends 82 each carry a snap fastener 62 of a design identical to that illustrated in FIG. 1. The enhancement of rotational stability is produced by the strap retaining sections 80 which prevent rotation of the bifurcated ends 82 within the loops 40 and 42. The increase in the number of attachment points of the clamp to the strap enhances lateral and longitudinal stability over that obtainable with the embodiment of FIGS. 1–4.

I claim:

1. An endotracheal tube holder for securing an endotracheal tube within a patient's mouth comprising:
   (a) a clamping means of variable diameter for permitting the securement of any one of a plurality of endotracheal tubes of different diameter in a patient's mouth without rotation of the tube with respect to said clamping means, said clamping means having a cylindrical section with an axis of rotation, an interior surface which is variable in diameter for securement to any one of said endotracheal tubes of different diameter, an exterior cylindrical surface whereby the thickness of the clamping means is minimized, a cut in said cylindrical section extending generally axially with respect to said axis of rotation of said cylindrical section to form first and second ends which may be displaced circumferentially from each other with respect to said axis of rotation of said cylindrical section and means for adjusting the circumferential displacement of the first and second ends from each other to permit clamping of said endotracheal tubes which range in diameter and first and second attachment means which are respectively attached to opposed sections of the exterior cylindrical surface for permitting securement of a strap to said exterior cylindrical surface of said cylindrical section, and
   (b) a strap having at least first and second ends, the first and second ends each respectively having first and second end attachment means which are respectively attachable to and detachable from the first and second attachment means, the width of the first and second end attachment means of the first and second ends in proximity to the patient's mouth being equal to or less than the outside diameter of the cylindrical section so as to not occlude access to and visualization of the patient's mouth.

2. An endotracheal tube holder in accordance with claim 1 further comprising first and second pads respectively secured in proximity to the first and second ends of the strap for contacting the patient's cheeks when an endotracheal tube is secured in the patients' mouth by the endotracheal tube holder to minimize skin irritation of the patient's cheeks.

3. A endotracheal tube holder in accordance with claim 2 wherein the first and second attachment means comprise at least a first and a second loop secured to opposed sections of the exterior cylindrical surface of the cylindrical section, the first loop being engaged by the first end of the strap and the second end being engaged by the second loop.

4. An endotracheal tube holder in accordance with claim 3 wherein:
   (a) the cylindrical section has first and second ends which respectively have first and second extensions joined thereto which project radially outward from the first and second ends; and
   (b) wherein the diameter of the clamping means is adjusted by said means for adjusting, said means for adjusting comprising:
      (i) a nut attached to the first extension, the nut having a threaded opening in alignment with a bore having keyway which is contained in the first extension to permit a threaded member to pass through the bore within the first extension and engage the threads of the nut;
      (ii) a threaded member having first and second ends, the threaded member engaging the threaded opening of said nut and having a key located at the first end, the threads of the threaded member extending from the second end toward the first end but not to the key so as to permit the key to extend through the bore of the nut and the first extension without engaging the threads of the nut, the second end having a head of a diameter larger than the diameter of the threaded member; and
      (iii) a bore contained within the second extension, the head of the threaded member being larger than the diameter of the bore of the second extension so that the head of the threaded member will be retained by the second extension when the threaded member engages the thread of the nut.

5. An endotracheal tube holder in accordance with claim 4 wherein the strap is comprised of first and second sections, the first end being at one end of the first section and the second end being at one end of the second section, the other end of the first section and the other end of the second section having first and second sections of material respectively attached thereto, the material having the characteristic that two surfaces of the material will adhere to each other upon surface contact.

6. An endotracheal tube holder in accordance with claim 5 wherein the first and the second end attachment means each have a snap fastener, closure of each snap fastener respectively forming third and fourth loops which respectively engage the first and second loops to secure the clamping means to the strap.

7. An endotracheal tube holder in accordance with claim 6 wherein the clamping means further comprises: a plurality of grooves in the interior surface of the cylindrical section which are disposed parallel to the longitudinal axis of the cylindrical section for gripping the endotracheal tube.

8. An endotracheal tube holder in accordance with claim 7 wherein:
the cylindrical section has first and second annular surfaces which have a padding material secured thereto.

9. An endotracheal tube holder in accordance with claim 2 wherein the first and second attachment means comprise:
(a) at least a first and a second loop secured to opposed sections of the exterior cylindrical surface of the cylindrical section, the first loop having first and second strap retaining sections respectively disposed near the points of juncture of the first loop with the exterior cylindrical surface of the cylindrical section which will retain a strap engaging the first and second strap retaining sections in a fixed angular position with respect to the first loop and the second loop having third and fourth strap retaining sections disposed near the points of juncture of the second loop with the exterior cylindrical surface of the cylindrical section which will retain a strap engaging the third and fourth strap retaining sections in a fixed angular position with respect to the second loop; and wherein
(b) the first end of the strap is bifurcated into two parts which respectively engage the first and second strap retaining sections and the second end of strap is bifurcated into two parts which respectively engage the third and fourth strap retaining sections.

10. An endotracheal tube holder in accordance with claim 8 wherein:
(a) the cylindrical section has first and second ends which respectively have first and second extensions joined thereto which project radially outward from the first and second ends; and
(b) wherein the diameter of the clamping means is adjusted by said means for adjusting, said means for adjusting comprising:
(i) a nut attached to the first extension, the nut having a threaded opening in alignment with a bore having keyway which is contained in the first extension to permit a threaded member to pass through the bore within the first extension and engage the threads of the nut;
(ii) a threaded member having first and second ends, the threaded member engaging the threaded opening of said nut and having a key located at the first end, the threads of the threaded member extending from the second end toward the first end but not to the key so as to permit the key to extend through the bore of the nut and the first extension without engaging the threads of the nut, the second end having a head of a diameter larger than the diameter of the threaded member; and (iii) a bore contained within the second extension, the head of the threaded member being larger than the diameter of the bore of the second extension so that the head of the threaded member will be retained by the second extension when the threaded member engages the thread of the nut.

11. An endotracheal tube holder in accordance with claim 10 wherein the strap is comprised of first and second sections, the first end being at one end of the first section and the second end being at one end of the second section, the other end of the first section and the other end of the second section having first and second sections of material respectively attached thereto, the material having the characteristic that two surfaces of the material will adhere to each other upon surface contact.

12. An endotracheal tube holder in accordance with claim 10 wherein the first and second end attachment means each have a snap fastener, closure of each snap fastener respectively forming third and fourth loops which respectively engage the first and second loops to secure the clamping means to the strap.

13. An endotracheal tube holder in accordance with claim 12 wherein the clamping means further comprises:
a plurality of grooves in the interior surface of the cylindrical section which are disposed parallel to the longitudinal axis of the cylindrical section for gripping the endotracheal tube.

14. An endotracheal tube holder in accordance with claim 13 wherein the cylindrical section has first and second annular surfaces which have a padding material secured thereto.

15. An endotracheal tube holder in accordance with claim 1, wherein the interior surface of said cylindrical section includes means for gripping endotracheal tubes which may vary in diameter securely to prevent rotation of said tubes with respect to said clamping means.

16. An endotracheal tube holder in accordance with claim 15, wherein the means for gripping comprises a plurality of grooves in the interior surface of the cylindrical section which are disposed generally parallel to the axis of rotation of said cylindrical section for gripping an endotracheal tube without slippage.

17. An endotracheal tube holder in accordance with claim 1, wherein the means for adjusting the circumferential displacement of the first and second ends comprises:
(a) first and second extensions joined respectively to the first and second ends, the first and second extensions projecting generally radially outward from the first and second ends, and
(b) means for varying the displacement between the first and second extensions to permit clamping of endotracheal tubes which may vary in diameter.

18. An endotracheal tube holder in accordance with claim 17, wherein the means for varying the displacement between the first and second extensions comprises:
(a) a threaded member having a stop at one end, and
(b) said first and second extensions each having a bore extending therethrough, one of said bores threadingly engaging the threaded member and the other bore being dimensioned to permit rotation of the threaded member without engaging the bore, the stop engaging the extension having the bore which does not threadably engage the threaded member whereby rotation of the threaded member varies the circumferential displacement between the first and second ends.

* * * * *